Oct. 14, 1958 E. S. BOERNER Plant Pat. 1,765
ROSE PLANT
Filed March 5, 1958
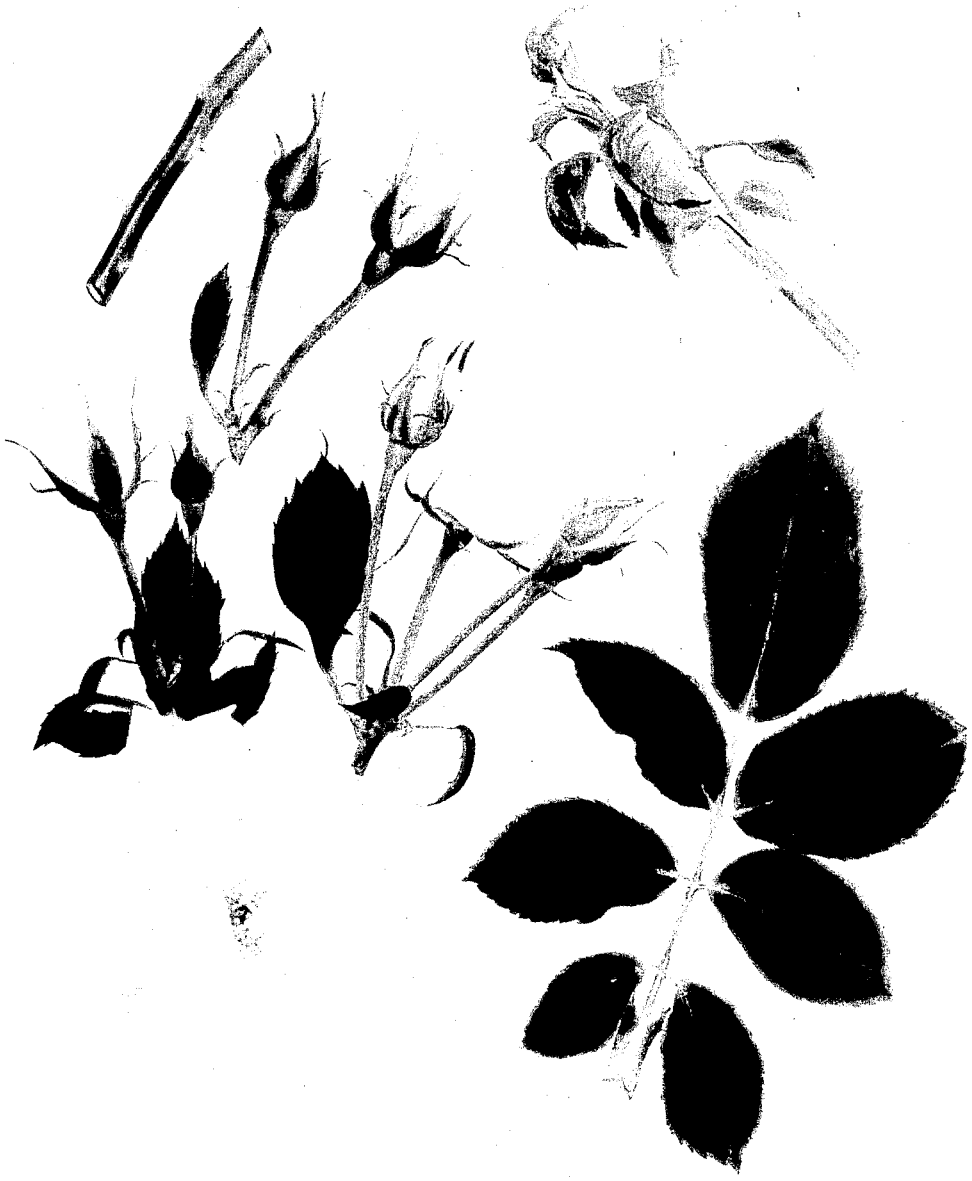
Inventor.
E. S. Boerner
By: Robb & Robb
Attorneys.

United States Patent Office

Plant Pat. 1,765
Patented Oct. 14, 1958

1,765

ROSE PLANT

Eugene S. Boerner, Newark, N. Y., assignor to Jackson & Perkins Company, Newark, N. Y., a corporation of New York Application March 5, 1958, Serial No. 719,465

1 Claim. (Cl. 47—61)

The present invention relates to a new and distinct variety of rose plant of the large-flowered polyantha class, which was originated by me by crossing an unnamed and unpatented seedling of "Pinocchio" (Plant Patent No. 484) with an unnamed and unpatented seedling of "Fashion" (Plant Patent No. 789).

The primary objective of this breeding was to produce a new rose variety of the floribunda class which has an upright and symmetrical growing habit. This objective was fully achieved, along with other desirable improvements, as evidenced by the following unique combination of characteristics which are outstanding in the new variety and distinguish it from its parents, as well as from all other varieties of which I am aware:

(1) Vigorous, upright and symmetrical habits of growth;

(2) Strong, stiff flower stems which make the variety especially suitable for cut flower purposes;

(3) Long-lasting flowers of exquisite shape; and (4) A distinctive La France Pink general color tonality of the flowers.

The seed parent of my new variety, seedling of "Pinocchio," was particularly characterized by its highly colored flowers, while the pollen parent, seedling of "Fashion," was outstanding for the beautiful shape of the plant and the coral color of its flowers. So far as I know, there has never been any floribunda rose having both an upright growth and symmetrical shape prior to my new variety.

Asexual reproduction of the new variety, by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.

*Seed parent.*—An unnamed seedling of "Pinocchio."

*Pollen parent.*—An unnamed seedling of "Fashion."

Classification:

*Botanic.*—Large-flowered polyantha.

*Commercial.*—Floribunda.

*Flower*

(Observations made from specimens grown in a greenhouse at Newark, New York, in the early afternoon during the latter part of August.)

Blooming habit: Recurrent—continuous.

Bud:

*Size.*—Small.

*Form.*—Ovoid; is not affected by wet or hot weather.

*Color.*—When sepals first divide—Geranium Pink, Plate 1. When petals begin to unfurl—Hermosa Pink, Plate 1. When half-brown: inside of petals —La France Pink, Plate 1, lightly overcast with Thulite Pink, Plate 26; reverse of petals—Thulite Pink, Plate 26, overcast with Hermosa Pink, Plate 1.

*Sepals.*—Branched; curl back when petals begin to unfurl. Color: inside—Kildare Green, Plate 31; outside—Biscay Green, Plate 17.

*Calyx.*—Color—Bice Green, Plate 17. Shape—funnel. Size—small. Aspect—smooth. Odor when rubbed—none.

*Peduncle.* — Length — medium. Aspect — rough. Strength—erect; slender. Color—Oil Green, Plate 5.

*Opening.*—Opens up well; is not affected by adverse weather conditions.

Bloom:

*Size.*—Medium. Average size when fully expanded—3½ inches.

*Borne.*—In pyramidal clusters.

*Stems.*—Medium length; strong; stiff.

*Form (when first open).*—Cupped. Permanence—retains its form to the end.

*Petalage.*—Double (full but open center). Number of petals under normal conditions—from 20 to 25.

*Color.*—Center of flower—La France Pink, Plate 1. Outer petals—Cameo Pink, Plate 26. Base of petals (aiglet)—Pale Green-Yellow, Plate 5. Inside of petals—Hermosa Pink, Plate 1, with lower half of petals lightly overcast with White, Plate 53. Reverse of petals—Rose Pink, Plate 12 on outer edges of petals, with center of petals lightly overcast with Hermosa Pink, Plate 1. General tonality from a distance—La France Pink, Plate 1.

*Discoloration.*—General tonality at end of first day—La France Pink, Plate 1. Second day—La France Pink, Plate 1. Third day—La France Pink, Plate 1, lightly overcast with Cameo Pink, Plate 26.

Petals:

*Texture.*—Thick; is not affected by wet or hot weather.

*Appearance.*—Inside—satiny. Outside—shiny.

*Form.*—Round.

*Arrangement.* — Imbricated (regularly arranged shingle-like).

*Petaloids in center.*—Few; large.

*Persistence.*—Drop off cleanly.

*Fragrance.*—Strong. Nature—"Old Rose perfume" (centifolia).

*Lasting quality.*—On the plant—very long. As cut flower—very long.

*Genital organs*

Stamens, anthers: Medium size; few; regularly arranged around styles. Color—Grenadine Red, Plate 2.

Stamens, filaments (threads): Medium length. Color—Begonia Rose, Plate 1.

Pollen: Color—Grenadine Pink, Plate 2.

Styles: Bunched; uneven length; short; thin.

Stigmas: Color—Capucine Orange, Plate 3.

Ovaries: All enclosed in calyx.

Hips: None.

Seeds: None.

*Plant*

Form: Bush.

Growth: Vigorous; upright; symmetrical.

Foliage: Compound of 3 to 7 leaflets.

*Size.*—Medium.

*Quantity.*—Abundant.

*Color.*—New foliage—upper side—Oil Green, Plate 5, with outer edges of leaf and serrations Garnet Brown, Plate 1; under side—Absinthe Green, Plate 31, lightly overcast with Oxblood Red, Plate 1. Old foliage: upper side—Dark Cress Green, Plate 31. under side—Bice Green, Plate 17.

*Shape.*—Oval pointed.

*Texture.*—Upper side—leathery. Under side—smooth.

*Ribs and veins.*—Ordinary.

*Edge.*—Serrated (saw-toothed).

*Serration.*—Both double and single; small.

*Leaf stem.*—Color—Courge Green, Plate 17. Under side—smooth.

*Stipules*—Medium length; bearded.

Wood:

*New wood.*—Color—Lettuce Green, Plate 5. Bark—smooth.

*Old wood.*—Color—Cress Green, Plate 31. Bark—smooth.

Thorns:

*Thorns.*—Quantity: on main stalks from base—few; on laterals from stalk—few. Form—narrow base; short; hooked downward. Color (when young)—Old Rose, Plate 13. Position—irregular.

*Prickles.*—Quantity: on main stalks—none; on laterals—none.

*Short needles.*—Quantity: on main stalks—none; on laterals—none.

I claim:

A new and distinct variety of rose plant of the large-flowered polyantha class, substantially as herein shown and described, characterized particularly as to novelty by the unique combination of vigorous, upright and symmetrical habits of growth, strong, stiff stems, with attendant suitability for cut flower purposes, long-lasting flowers of exquisite shape, and the distinctive La France Pink general color tonality of the flowers.

No references cited.